United States Patent [19]

Commereuc

[11] Patent Number: 5,747,408
[45] Date of Patent: May 5, 1998

[54] SUPPORTED CATALYSTS CONTAINING RHENIUM AND ALUMINIUM, PREPARATION THEREOF AND USE THEREOF FOR THE METATHESIS OF OLEFINS

[75] Inventor: Dominique Commereuc, Meudon, France

[73] Assignee: Institut Francais du Petrole, Rueil-Malmaison, France

[21] Appl. No.: 554,351

[22] Filed: Nov. 6, 1995

[30] Foreign Application Priority Data

Nov. 4, 1994 [FR] France .................. 94 13349

[51] Int. Cl.$^6$ .................. B01J 31/00; C07C 6/00
[52] U.S. Cl. .................. 502/171; 502/150; 502/168; 502/170; 502/172; 502/355; 502/102; 585/647; 585/643
[58] Field of Search .................. 502/150, 168, 502/170, 171, 172, 355, 102; 585/647, 643

[56] References Cited

U.S. PATENT DOCUMENTS

| | | | |
|---|---|---|---|
| 4,454,368 | 6/1984 | Banks | 585/646 |
| 4,943,397 | 7/1990 | Johnson | 260/405.5 |
| 5,135,958 | 8/1992 | Radlowski et al. | |
| 5,218,131 | 6/1993 | Warwel et al. | 554/163 |
| 5,342,985 | 8/1994 | Hermann et al. | 556/481 |
| 5,405,924 | 4/1995 | Kelsey | 526/142 |
| 5,449,852 | 9/1995 | Chauvin et al. | 585/647 |

FOREIGN PATENT DOCUMENTS

| | | |
|---|---|---|
| 0 313 283 | 4/1989 | European Pat. Off. . |
| 0 444 265 | 9/1991 | European Pat. Off. . |

*Primary Examiner*—Glenn Caldarola
*Assistant Examiner*—Thuan D. Dang
*Attorney, Agent, or Firm*—Millen, White, Zelano, & Branigan, P.C.

[57] ABSTRACT

The present invention concerns new catalysts based on compounds containing both rhenium and aluminum, which are deposited on an organic or inorganic support. The compounds of rhenium and aluminum correspond to the general formula:

$$O_3Re-O-[Al(OR)(L)_x-O]_n-ReO_3$$

in which R is a hydrocarbyl residue, for example alkyl, cycloalkyl, alkenyl, aryl, and aryl or cycloalkyl which are substituted, containing from 1 to 40 carbon atoms, which residue can be substituted by alkoxy groups or by halogens, L is the synthesis solvent, x is equal to 0 or 1 and n is an integer of from 1 to 10. The invention also concerns the preparation of such catalysts and the use thereof for the metathesis of olefins.

21 Claims, No Drawings

SUPPORTED CATALYSTS CONTAINING RHENIUM AND ALUMINIUM, PREPARATION THEREOF AND USE THEREOF FOR THE METATHESIS OF OLEFINS

BACKGROUND OF THE INVENTION

The present invention concerns new supported catalysts containing rhenium and aluminium, the preparation thereof and the use thereof for the metathesis of olefins.

There are not many rhenium-based supported catalysts which are active for the reaction for the metathesis of olefins. The oldest and most generally used is rhenium heptoxide deposited on inorganic oxides, in most cases alumina (British patent No. 1,054,864) but also on supports comprising both alumina and another co-oxide (R. Nakamura, Rec. Trav. Chim. Pays-Bas, Vol 96, 1977, page M31). The use of organometallic co-catalysts such as tetraalkyltins associated with the catalyst comprising rhenium oxide on alumina permits, amongst other advantages, the metathesis of functional olefins (J. C. Mol, C Boelhouwer et al., J. Chem Soc Chem Comm, 1977, page 198). W Herrmann claimed the use of complexes such as methyltrioxorhenium and pentamethylcyclopentadienyl-trioxorhenium which are deposited on various inorganic oxides including in particular alumina and silica-aluminas (Hoechst, European patents Nos. 373,488 and 522,067).

SUMMARY OF THE INVENTION

The present invention describes new catalysts based on compounds containing both rhenium and aluminium, which are deposited on an organic or inorganic support, and which constitute excellent catalysts for the metathesis of olefins.

More precisely the invention concerns a supported catalyst containing at least one compound of rhenium and aluminium, of the general formula:

$$O_3Re-O-[Al(OR)(L)_x-O]_n-ReO_3$$

wherein R is a hydrocarbyl residue containing from 1 to 40 carbon atoms, L is the synthesis solvent, x is equal to 0 or 1 and n is an integer from 1 to 10.

Those compounds of rhenium and aluminium correspond to the general 30 formula:

$$O_3Re-O-[Al(OR)(L)_x-O]_n-ReO_3 \quad (A)$$

wherein R is a hydrocarbyl residue, for example alkyl, cycloalkyl, alkenyl, aryl, and aryl or cycloalkyl which are substituted, containing from 1 to 40 carbon atoms, preferably a hydrocarbyl residue with from 2 to 30 carbon atoms, which residue can be substituted by at least one alkoxy group or at least one halogen, L is the synthesis solvent, x is equal to 0 or 1 and n is an integer of from 1 to 10. By way of example and without the list being limitative, R may be an ethyl, n-propyl, isopropyl, n-butyl, t-butyl, cyclohexyl, benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenyl, 2-t-butyl-4-methylphenyl, 2,6-di-t-butylphenyl, 2,6-di-tbutyl-4-methylphenyl, 2,4,6-tri-t-butylphenyl, 2-phenylphenyl, 2,6-diphenylphenyl, 2-fluorophenyl, 4-fluorophenyl and pentafluorophenyl residue.

The solvent L will be defined hereinafter in the description of a preparation process.

Those compounds of rhenium and aluminium are unstable, as they are in themselves active for example for olefins metathesis catalysis. In order to characterize them it is necessary to stabilize them by the addition of suitable ligands at the end of their synthesis. The stabilized compounds which are inactive in respect of catalysis correspond to the following general formula:

$$O_3Re(L')-O-[Al(OR)(L)_x-O]_n-ReO_3(L') \quad (B)$$

wherein L' is a stabilizing ligand selected from the compounds comprising at least one atom of oxygen, sulphur, nitrogen, phosphorous or arsenic, for example an ether such as diethylether, 1,2-dimethoxyethane or tetrahydrofuran, a sulphide such as tetrahydrothiophene, an amine such as triethylamine, pyridine, 2,2-'bipyridine or N,N,N',N'-tetramethylethylenediamine, a phosphine such as triphenylphosphine or 1,2-bis-(diphenylphosphino)-ethane. R, L, x and n have been defined in the expression of the formula of compound A.

Identification of the stabilized compounds B makes it possible to characterize the compounds A a posteriori: the formula of A is deduced from that of B by abstraction of the stabilising ligand L'. Moreover, by de-co-ordination of L', the compound A can be obtained from compound B.

The compounds of rhenium and aluminium which are used in the invention are synthesized by the reaction between rhenium heptoxide $Re_2O_7$ and at least one compound of aluminium of the formula $(RO)_qAlR'_r$ wherein R is as defined above, R' is an alkyl residue containing from 1 to 20 carbon atoms, preferably from 1 to 6 carbon atoms, for example methyl, ethyl or isobutyl, q and r are equal to 1 or 2 in such a way that the sum q+r is equal to 3.

The reaction is effected in a solvent L which is preferably anhydrous and which is selected from the group formed by aliphatic or aromatic hydrocarbons such as, for example, pentane, hexane, benzene, toluene, halogenated hydrocarbons such as, for example, dichloromethane, chlorobenzene, ethers such as, for example, diethylether, diisopropylether, 1,2-dimethoxyethane, tetrahydrofuran or sulphides such as tetrahydrothiophene. An ether is preferably used. Said solvent L as defined may be included in the general formula of compounds A.

The molar ratio between the aluminium compound and the rhenium may be selected at from 0.2:1 to 10:1. A ratio of 0.5:1 to 5:1 is preferably used. The order in which the reactants are introduced is not critical, however it is preferable for the aluminium compound to be introduced in the solution or the suspension of rhenium heptoxide.

Preparation of the compound $(RO)_qAlR'_r$ is known to the man skilled in the art. Any process for the preparation of that compound is suitable, for example, by the reaction of at least one compound $AlR'_3$ with at least one compound ROH. R and R' being as defined above, the reaction advantageously taking place in the solvent L. The compound prepared in that way is brought into contact with rhenium heptoxide. Generally speaking, the compound prepared in that way is isolated and then brought into contact with rhenium heptoxide under the conditions described by the invention.

In another embodiment the reactants used to form the compound $(RO)_qAlR'_r$ are simultaneously brought into contact with rhenium heptoxide without therefore separation of the product $(RO)_qAlR'_r$.

Thus the catalyst is prepared in accordance with the process in which the rhenium heptoxide is reacted with at least one compound of the formula $AlR'_3$ in which R' is an alkyl residue containing from 1 to 20 carbon atoms and with at least one compound of the formula ROH, R being a hydrocarbyl residue containing from 1 to 40 carbon atoms, the reaction occurring in a solvent L, and the mixture obtained is deposited on the support, and the product obtained is dried.

The reaction temperature can be from −80 to +100° C., preferably from −30 to +80° C. When the reaction is terminated the solvent is advantageously at least partially eliminated (for example the solvent is evaporated under vacuum) and the (evaporation) residue is extracted by a solvent $L_1$, for example an aliphatic, aromatic or cycloaliphatic hydrocarbon, or again a halogenated hydrocarbon or a nitro derivative, such as for example advantageously pentane, heptane, benzene or toluene. The extraction solution can be used directly for preparation of the supported catalyst.

In accordance with an alternative configuration the solution obtained containing the compound A is directly used for preparation of the supported catalyst. Previous separation of the solvent is also possible in this case.

If there is a wish to isolate a stable compound B which permits characterisation a posteriori of the compound A present in the extraction solution, added to the latter is the ligand L' as defined above, and the stabilised compound B is separated by any usual method, for example by precipitation or crystallisation.

The compounds of rhenium and aluminium as described hereinbefore are deposited on organic or inorganic supports (alone or in the form of a mixture) by impregnation of the support with the solution obtained at the end of preparation thereof, and preferably with the extraction solution.

The organic supports are generally polymers or copolymers which may or may not be cross-linked and among which mention may be made of the following by way of example, without the list being limitative: polystyrene which may or may not be functionalised by groups: alcohol, ether, phenol, amine, phosphine, which is possibly cross-linked to variable degrees for example by divinylbenzene, polyvinylchloride, polyethylene, polybutadiene, which may or may not be grafted by functional groups, polyethers such as polyethyleneglycols and derivatives thereof, polyamides, polyacrylonitrile, polyvinyl-pyridine, polyvinyl-pyrrolidinone, and natural polymers such as cellulose or starch.

The inorganic supports are formed by refractory oxides and/or alumino-silicates which may be of an acid, neutral or basic character. The following may be mentioned by way of example, without the list being limitative: alumina, silica, silica-aluminas, zeolites, titanium oxide, zirconia, niobium oxide, chromium oxide, magnesia and tin oxide.

The support used is preferably an inorganic support of acid or neutral character, more particularly an alumina, a silica or a silica-alumina, with a specific surface area of from 10 to 400 $m^2/g$. The support must first be cleared of any trace of water and air, for example by a roasting treatment followed by cooling with a sweep flow of an inert gas such as nitrogen or argon.

The impregnation method is not critical but it is imperative to operate protected from air and moisture. The support can be impregnated by an excess of the solution, preferably the extraction solution, containing the compound A, which was obtained at the end of the reaction between rhenium heptoxide and the compound of aluminium (RO)$_q$AlR'$_r$. After a contact time which may range from a few minutes to a few days, the solid is dried without heating and it is washed with the solvent to remove the portion of the compound which is not fixed. Also, in an operating mode which is preferred, it is possible to use the dry impregnation method. In that case the concentration of rhenium in the solution is adjusted in dependence on the amount of rhenium which is to be deposited on the support, in such a way that the volume of that solution is equal to or slightly less than the pore volume of the sample of the support to be impregnated. The impregnation step can be terminated by a drying operation, under vacuum or a flow of gas which is preferably inert, at a temperature of from 0 to 1000° C., preferably from 0 to 200° C.

The invention therefore also concerns a process for the preparation of supported catalysts containing at least one compound of rhenium and aluminium of the following general formula:

wherein R is a hydrocarbyl radical containing from 1 to 40 carbon atoms, L is a solvent, x is equal to 0 or 1 and n is an integer of from 1 to 10, wherein said compound of rhenium and aluminium is prepared by reacting rhenium heptoxide with a compound of aluminium of the formula (RO)$_q$AlR'$_r$, wherein R' is an alkyl residue containing from 1 to 20 carbon atoms, q and r are equal to 1 or 2 and the sum q+r is equal to 3, the reaction occurring in a solvent L, at a temperature of from −80 to +100° C., and with a molar ratio between the aluminium compound and the rhenium of between 0.2:1 and 10:1, then said compound is deposited on the support, and the product obtained is dried.

The compound of aluminium and rhenium is therefore deposited on the support by means of a solution of said compound in the solvent L used for preparation of said compound, and/or preferably by means of a solution of said compound in the extraction solvent $L_1$.

The present invention further concerns the use of such compounds of rhenium and aluminium which are deposited on a support as catalysts for the metathesis reaction of olefins. No chemical or thermal activation operation is required to initiate the activity of such catalysts. It is only necessary for them to be brought into contact with an olefin for the metathesis reaction to start.

Although however this is not essential, it is possible to add to the catalyst at least one co-catalyst having alkylating and/or Lewis acid properties. The co-catalyst may be a compound of aluminium, boron, gallium, tin or lead. By way of example, and without the list being limitative, mention may be made of aluminium trichloride, aluminium tribromide, dichloroethylaluminium, chlorodiethylaluminium, triethylaluminium, methylaluminoxane, isobutylaluminoxane, boron trifluoride, gallium trichloride, gallium tribromide, tetramethyltin, tetraethyltin, tetrabutyltin and tetraethyllead. It is also possible to use those various compounds mixed with each other. The co-catalyst can be introduced on to the catalyst prior to the metathesis operation, for example by impregnation by means of one of the methods described above, or during the metathesis operation, the co-catalyst then being mixed with the olefins.

The invention also concerns a process for the metathesis of olefins in the presence of the above-defined catalyst at a temperature of from −20 to +200° C., preferably from 0 to +100° C., under pressure conditions which are variable depending on whether the reaction is to be conducted in the gaseous phase or in the liquid phase.

In an operation in the liquid phase the pressure is to be sufficient for the reactants and the solvent if provided to be maintained at least in respect of the majority thereof (more than 50%) in the liquid phase (or in a condensed phase). The catalyst can then be used either in the pure olefin (or olefins), or in the presence of a solvent formed by an aliphatic, cycloaliphatic or aromatic hydrocarbon, a halogenated hydrocarbon or a nitro derivative. A hydrocarbon or a halogenated hydrocarbon are preferably used.

The olefins which are capable of being metathesized are monoolefins having from 2 to 30 carbon atoms, for example ethylene, propylene, butenes and pentenes, cycloolefins having from 3 to 20 carbon atoms, for example cyclopentene, cyclooctene and norbornene, polyolefins having from 4 to 30 carbon atoms, for example hexa-1,4-diene, octa-1,7-diene, and cyclopolyolefins having from 5 to 30 carbon atoms, for example cycloocta-1,5-diene, norbornadiene and dicyclopentadiene.

Other olefins which are capable of being metathesized, are monoolefins or polyolefins, which are in straight-chain or ring form, bearing functional groups such as for example halogens or ester groups. The process may also use in a co-metathesis operation a mixture of the foregoing olefins.

The following Examples illustrate the invention without limiting the scope thereof.

EXAMPLES

Example 1

Preparation of bis-(2,6-di-t-butyl-4-methylphenoxy)-isobutylaluminium:

Using a 250 ml balloon flask disposed in an argon atmosphere and provided with a magnetic stirrer rod, a solution of 2 ml of triisobutylaluminium in 30 ml of pentane is introduced, and then a solution of 3.49 g of 2,6-di-t-butyl-4-methylphenol in 40 ml of pentane is introduced dropwise with agitation and at ambient temperature. After about 30 hours of reaction the pentane is evaporated under vacuum and analysis of the white solid remaining indicates that it is formed essentially by bis-(2,6-di-t-butyl-4-methylphenoxy)-isobutylaluminium.

Preparation of the compound of rhenium and aluminium (compound A):

Using a 250 ml balloon flask in an argon atmosphere and provided with a magnetic stirrer rod, the procedure involves introducing 2.75 g of rhenium heptoxide $Re_2O_7$ which is dissolved in 40 ml of tetrahydrofuran (THF). The solution is cooled in a solid carbon dioxideace-tone bath and a solution of 2.97 g of bis-(2,6-di-t-butyl-4-methylphenoxy)-isobutylaluminium in 50 ml of tetrahydrofuran is added thereto over a period of 30 minutes. That corresponds to an Al: Re molar ratio of 0.5:1. At the end of the addition operation the temperature is allowed to rise to ambient temperature and agitation is continued for a further 2 hours. The solvent is then evaporated under vacuum to produce a grey-black solid mass which is then extracted five times with 30 ml of pentane. The pentane extraction solution is of a brown-red colour and evaporation thereof to dryness gives 3.32 g of a brown powder containing the compound A. That powder is put back into solution in 30 ml of heptane.

Characterization of the compound of rhenium and aluminium (compound B):

4.5 ml of the solution in heptane of the compound A prepared above is taken off. The solvent is evaporated to dryness and 10 ml of toluene is used to produce a new solution. 0.11 g of 2,2'bipyridine(bipy) dissolved in 3 ml of toluene is added to that solution. By cooling to −20° C., 0.1 g of compound B is obtained in the form of black microcrystals. Analysis by NMR $^1H(CD_2Cl_2):\delta[C(CH_3)_3]=1.40$ (s), $\delta(p\text{-}CH_3)=2.23\delta(C_6H_2)$–6.95, δ(co-ordinated bipy)= 7.32–7.81–8.41–8.64 ppm. Elementary analysis: C=47.46; H=5.66; N=3.17; Al=4.33; Re=26.4% by weight, calculated for B: $O_3Re(bipy)$—O—[$Al(OC_6H_2$—$CH_3$—$(t$—$C_4H_9)_2$) (THF)—O]$_2$—$ReO_3$(bipy):C=47.54; H=5.33; N=3.82; Al=3.69; Re=25.4% by weight. It is deduced therefrom that compound A prepared above corresponds to the formula:

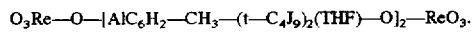

Example 2

Preparation of the supported catalyst:

The support used is a gamma alumina in ball form having a specific surface area of 180 m$^2$/g and a pore volume of 0.55 ml/g. 18.2 g of that alumina is loaded into a Pyrex tube with a usable volume of 100 ml, which is disposed in a vertical oven, and it is roasted at 550° C. in a flow of air containing less than 300 ppm by weight of water, at a rate of 25 l/h when adjusted to normal conditions, for a period of 2 hours. At the end of that period and before beginning cooling, the flow of air is replaced by a flow of nitrogen containing less than 30 ppm of water and the alumina is then allowed to cool down under those conditions.

The alumina is then transferred into a 100 ml balloon flask disposed in an argon atmosphere, and 10 ml of the solution in heptane of the compound A prepared in Example 1 is injected into the balloon flask, with manual agitation thereof. The solution is completely absorbed by the alumina. After one hour the catalyst is dried under vacuum at ambient temperature. The balls are of a brown-red coloring and are preserved in an argon atmosphere. The rhenium content of the catalyst is 2.2% by weight.

Example 3

Use of the catalyst for metathesis of pent-2-ene:

5.5 g of the catalyst prepared in Example 2 is taken off in an argon atmosphere and transferred into a 100 ml balloon flask provided with a magnetic stirrer rod and immersed in a thermostatically controlled bath at 25° C. 5 ml of heptane and then 3 ml of pent-2-ene (cis+trans mixture) are then introduced into the balloon flask. After 4 minutes of reaction conversion of the pent-2-ene is 26% and after 15 minutes of reaction it is 50% (which represents the maximum conversion at thermodynamic equilibrium). The products are formed solely by cis and trans but-2-enes and cis and trans hex-3-enes in a butenes:hexenes molar ratio of 1:1.

The catalyst is left for one week at ambient temperature in contact with the mixture of heptane, butenes, pentenes and hexenes resulting from the above-described test. After that period of time the liquid is drawn off and the catalyst is rinsed with 3 times 20 ml of heptane. The balloon flask containing the catalyst is then again imersed in a thermostatically controlled bath at 25° C. 5 ml of heptane and then 3 ml of pent-2-ene (cis+trans mixture) are again injected therein. After 5 minutes of reaction conversion of the pent-2-ene is 32% and after 15 minutes of reaction it is 48%. The products are formed solely by cis and trans but-1-enes and cis and trans hex-3-enes in a butenes:hexenes molar ratio of 1:1. This second test shows that the catalyst is practically not deactivated at the end of a week.

At the end of this second test the solution is drawn off and the catalyst is briefly dried under vacuum then put back into an argon atmosphere and preserved in that condition at ambient temperature for two months. After that period of time the balloon flask containing the catalyst is again immersed in a thermostatically controlled bath at 25° C. 5 ml of heptane and then 3 ml of pent-2-ene (cis+trans mixture are again injected into the balloon flask. After 15 minutes of reaction the conversion is 48%. The products are formed solely by cis and trans but-2-enes and cis and trans hex-3-enes in a butenes:hexenes molar ratio of 1:1. This third test shows that the catalyst is practically not deactivated after 2 months.

I claim:

1. A catalyst comparising a support and at least one rhenium/aluminum compound of the formula:

$$O_3Re—O—[Al(OR)(L)_x—O]_n—ReO_3$$

wherein R is an aryl residue of up to 40 carbon atoms, optionally substituted by at least one alkyl group, alkoxy group or halogen, L is synthesis solvent, x is equal to 0 or 1 and n is an integer of from 1 to 10.

2. A catalyst according to claim 1 wherein R is selected from the group formed by the residues: alkyl, cycloalkyl, alkenyl, aryl, and aryl or cycloalkyl which are substituted by at least one alkyl group.

3. A catalyst according to claim 1, wherein R is aryl optionally substituted by at least one alkyl group, and substituted by at least one alkoxy group or at least one halogen.

4. A catalyst according to claim 1, wherein R contains up to 30 carbon atoms.

5. A catalyst according to claim 1, wherein R is benzyl, diphenylmethyl, phenyl, 2-methylphenyl, 4-methylphenyl, 2-methoxyphenyl, 4-methoxyphenyl, 2,6-dimethylphenyl, 2,6-diisopropylphenyl, 2-t-butylphenyl, 2-t-butylphenyl, 2-t-butyl-4-methylphenyl, 2,6-di-t-butylphenyl, 2,6-di-t-butyl-4-methylphenyl, 2,4,6-tri-t-butylphenyl, 2-phenylphenyl, 2,6-diphenylphenyl, 2-fluorophenyl, 4-fluorophenyl or pentafluorophenyl.

6. A catalyst according to claim 1, wherein L is an aliphatic hydrocarbon, an aromatic hydrocarbon, a halogenated hydrocarbon, an ether or a sulphide.

7. A catalyst according to claim 1, wherein the support is a polymer, copolymer, cross-linked polymer, cross-linked copolymer, polymer which is grafted by functional groups, a copolymer which is grafted by functional groups, a natural polymer, a refractory oxide, an alumino-silicate, or a mixture thereof.

8. A catalyst according to claim 7 wherein the support has a specific surface area of from 10 to 400 m²/g is alumina, silica, or silica-alumina.

9. A process for the preparation of a catalyst according to claim 1 comprising preparing the compound of rhenium and aluminium by reacting rhenium heptoxide with a compound of aluminium of the general formula (RO)$_q$AlR'$_r$ wherein R' is an alkyl residue containing from 1 to 20 carbon atoms, q and r are equal to 1 or 2 and the sum q+r is equal to 3, the reaction occurring in a solvent L, at a temperature of from −80 to +100° C., and with a molar ratio between the aluminium compound and the rhenium of between 0.2:1 and 10:1, said compound being deposited on the support.

10. A process for the preparation of a catalyst according to claim 1 comprising reacting rhenium heptoxide with at least one compound of the formula AlR'$_3$ wherein R' is an alkyl residue containing from 1 to 20 carbon atoms and with at least one compound of the formula ROH, R being an aryl or cycloaryl residue containing up to 40 carbon atoms, the reaction occurring in a solvent L.

11. A preparation process according to claim 9 wherein the solvent L is anhydrous.

12. A process according to claim 9, wherein said compound of rhenium and aluminum is deposited by impregnation of the support by a solution of said compound.

13. A process according to claim 9, wherein said compound deposited on the support is in solution in the synthesis solvent L used in preparation of said compound.

14. A process according to claim 9, wherein after said compound of rhenium and aluminum in the solvent L has been prepared, said solvent is at least partially eliminated and the residue obtained is extracted with a solvent L$_1$, and said compound in solution in the solvent L$_1$ is then deposited on the support.

15. A process for the metathesis of olefins comprising subjecting olefins to metathesis conditions in the presence of a catalyst obtained in accordance with claim 1.

16. A process according to claim 15, wherein the olefins are monoolefins having from 2 to 30 carbon atoms, cycloolefins having from 3 to 20 carbon atoms, polyolefins having from 4 to 30 carbon atoms, cyclopolyolefins having from 5 to 30 carbon atoms, monoolefins having form 2 to 30 carbon atoms and bearing functional groups which are halogens and ester groups, or polyolefins having from 4 to 30 carbons atoms and bearing functional groups which are halogens or ester groups.

17. A process according to claim 15 wherein the olefins are ethylene, propylene, butenes, pentenes, cyclopentene, cyclooctene, norbonene, hexa-1,4-diene, octa-1,7-diene, cycloocta-1,5-diene, norbonadiene, dicyclopentadiene or methyl oleate.

18. A process according to claim 15 conducted in the presence of at least one co-catalyst having alkylating and/or Lewis acid properties.

19. A process according to claim 18 wherein said co-catalyst is an aluminum compound, a boron compound, a gallium compound a tin compound or a lead compound.

20. A process according to claim 18 wherein said co-catalyst is aluminum trichloride, aluminium tribromide, dichloroethylaluminium, chlorodiethylaluminium, triethylaluminium, methylaluminoxane, isobutylaluminoxane, boron trifluoride, gallium trichloride, gallium tribromide, tetramethyltin, tetraethyltin, tetrabutyltin or tetraethyllead.

21. A process according to claim 9, further comprising drying the product obtained.

* * * * *